(12) United States Patent
Krell et al.

(10) Patent No.: US 7,700,784 B2
(45) Date of Patent: Apr. 20, 2010

(54) COUPLING REACTIONS USEFUL IN THE PREPARATION OF (1H-TETRAZOL-5-YL) BIPHENYL DERIVATIVES

(75) Inventors: Christoph Krell, Basel (CH); Hans Hirt, Reinach (CH)

(73) Assignee: Novartis AG, Basel (CH)

( * ) Notice: Subject to any disclaimer, the term of this patent is extended or adjusted under 35 U.S.C. 154(b) by 726 days.

(21) Appl. No.: 10/588,169

(22) PCT Filed: Feb. 1, 2005

(86) PCT No.: PCT/EP2005/000978

§ 371 (c)(1),
(2), (4) Date: Aug. 2, 2006

(87) PCT Pub. No.: WO2005/075462

PCT Pub. Date: Aug. 18, 2005

(65) Prior Publication Data

US 2007/0129413 A1    Jun. 7, 2007

(30) Foreign Application Priority Data

Feb. 2, 2004    (GB) ................... 0402262.0

(51) Int. Cl.
C07D 257/04    (2006.01)
(52) U.S. Cl. ..................... 548/252; 548/250
(58) Field of Classification Search ............. 548/250, 548/252
See application file for complete search history.

(56) References Cited

U.S. PATENT DOCUMENTS

| 4,874,867 | A |   | 10/1989 | Aldrich et al. |
| 5,206,374 | A | * | 4/1993  | Lo ............. 548/110 |
| 5,310,928 | A | * | 5/1994  | Lo et al. ............. 548/252 |
| 5,371,233 | A |   | 12/1994 | Daumas et al. |
| 5,468,867 | A | * | 11/1995 | Fisher et al. ............. 548/253 |
| 7,038,060 | B2 | * | 5/2006 | Dolitzky et al. ............ 548/253 |
| 2004/0028962 | A1 |   | 2/2004 | Stolten et al. ............. 429/13 |

FOREIGN PATENT DOCUMENTS

| EP | 0550 313 | 7/1993 |
| FR | 2688503 A | 3/1992 |
| WO | WO 96/13489 A | 5/1996 |
| WO | WO 2004/026847 A1 * | 4/2004 |
| WO | WO 2005/005462 A | 8/2005 |

OTHER PUBLICATIONS

Miller et al., Tetrahedron Letters 39, pp. 7275-7278, "Synthesis of Functionally Substituted Unsymmetrical Biaryls via a Novel Double Metal Catalyzed Coupling Reaction" (1998).
Database Beilstein, Ekhato, V.I. et al, XP002327684, Data base accession No. 6833145.
Bradbury, R. H., et al, Journal of Medicinal Chemistry, vol. 35, No. 22, Oct. 30, 1992, pp. 4027-4038, XP000670277.
Ekhato I. Victor et al., "Model Reactions Targeted at the Synthesis of Carbon-14 Labeled CI-996, a Potent Antagonist of Angiotensin II Receptor," Journal of Labelled Compounds and Radiopharmaceuticals, vol. XXXIV, No. 3, pp. 213-220 (1994).

* cited by examiner

Primary Examiner—Golam M Shameem
(74) Attorney, Agent, or Firm—Joseph T. Majka

(57) ABSTRACT

The present invention relates to a process for the manufacture of intermediates that may be used for the manufacture of ARBs (also called angiotension II receptor antagonists or AT1 receptor antagonists) comprising as a common structural feature a (1H-tetrazol-5-yl)-biphenyl ring.

16 Claims, No Drawings

COUPLING REACTIONS USEFUL IN THE PREPARATION OF (1H-TETRAZOL-5-YL) BIPHENYL DERIVATIVES

This application is the National Stage of Application No. PCT/EP2005/000978, filed on Feb. 1, 2005, which claims benefit under 35 U.S.C. 119(a)-(d) of Great Britain Application No. 0402262.0, filed Feb. 2, 2004. The contents of both are incorporated herein by reference in their entirety.

The present invention relates to a process for the manufacture of intermediates that may be used for the manufacture of ARBs (also called angiotension II receptor antagonists or AT, receptor antagonists) comprising a tetrazole ring as a common structural feature. ARBs can, for example, be used for the treatment of hypertension and related diseases and conditions.

For example, mention may be made of ARBs that are selected from the group consisting of valsartan (cf. EP 443983), losartan (cf. EP 253310), candesartan (cf. EP 459136), eprosartan (cf. EP 403159), irbesartan (cf. EP 454511), olmesartan (cf. EP 503785), and tasosartan (cf. EP 539086), or, in each case, a pharmaceutically acceptable salt thereof.

More specifically, all these ARBs comprise the following common structural element of formula (A):

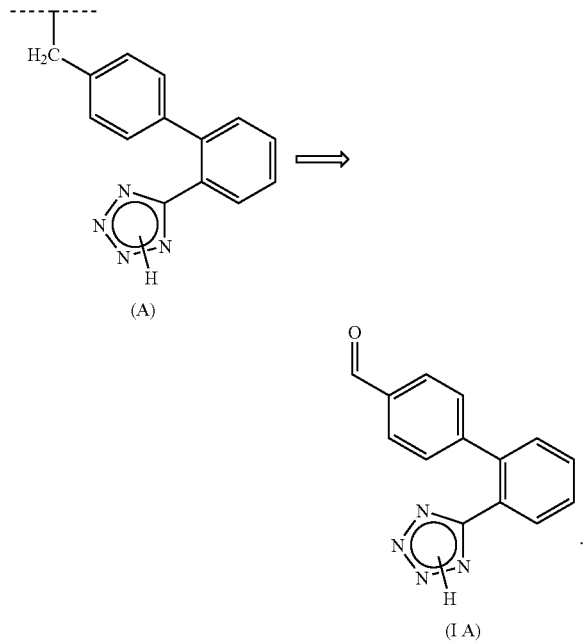

The manufacture of an aldehyde of formula (I A), corresponding to said element of formula (A), is a critical step in the manufacture of the above-mentioned angiotensin II receptor antagonists. Various aryl-aryl coupling reactions to form the biphenyl moiety in an aldehyde of formula (I A) have been recommended in the art.

EP 550313 describes the preparation of protected 2'-(1H-tetrazol-5-yl)-biphenyl-4-carbaldehyde involving transition metal catalyzed coupling of protected 5-(2-iodophenyl)-2H-tetrazole with an organozinc reagent or an arylboronic acid. The formation of stoichiometric quantities of zinc salt waste in the first case, and the several chemical steps required for the preparation of the arylboronic acid in the second case, and the formation of stoichiometric quantities of iodide waste in both cases are regarded as disadvantages.

U.S. Pat. No. 5,468,867 discloses the preparation of protected 2'-1H-tetrazol-5yl)-biphenyl-4-carbaldehyde involving metallation of an arylhalide with an organometallic base such as an alkyllithium reagent followed by coupling, e.g., with protected 5-(2-methoxyphenyl)2H-tetrazole. A disadvantage of this procedure is the formation of stoichiometric quantities of reactive, halogen containing waste.

The objective of the present invention is to provide a novel synthesis for compounds of formulae (I) and (I C)

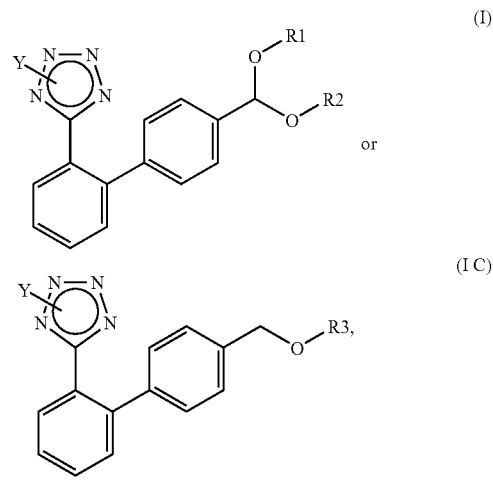

wherein Y is a tetrazole protecting group, $R_1$ and $R_2$, independently of one another, represent $C_1$-$C_{10}$-alkyl, or $R_1$ and $R_2$ combined together form $C_2$-$C_{10}$-alkylene, and $R_3$ represents a hydroxyl protecting group; that (1) does not have the disadvantages described above, (2) allows for the use of such tetrazole protecting groups which are easily removed in the presence of a Bronsted acid, (3) does not require large excesses of reagents, (4) gives high yields, (5) gives a minimum of waste, especially no stoichiometric amounts of reactive or environmentally problematic waste, and (6) is economically attractive.

Compounds of formulae (I) and (I C) may be easily converted to compounds of formula (I A) and, therefore, are important intermediates for the manufacture of ARBs having the structural feature corresponding to formula (A), as described, e.g., in International PCT Application No. WO 04/026847.

It has surprisingly been found that the process according to the present invention meets at least the above objectives.

In one aspect, the present invention relates to a process for the manufacture of a compound of formula (I)

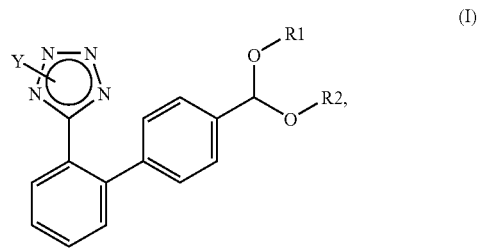

wherein Y represents a tetrazole protecting group, and R₁ and R₂, independently of one another, represent C₁-C₁₀-alkyl, or R₁ and R₂ combined together form C₂-C₁₀-alkylene; comprising (a) reacting a compound of formula (II a)

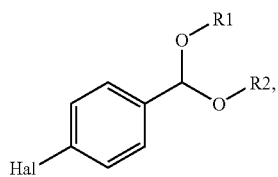

(II a)

wherein Hal is chlorine, bromine or iodine, with an active form of magnesium in an appropriate solvent;

(b) reacting a resulting aryl magnesium halide compound of formula (II b)

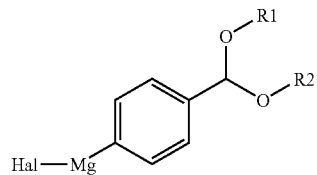

(II b)

in the presence of a transition metal catalyst and a catalytically effective amount of a metal salt additive, with a compound of formula (II c)

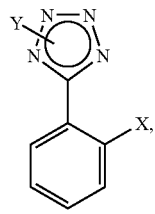

(II c)

wherein X is a substituent which, when bound to a phenyl ring, is not considerably replaceable at room temperature by an arylmagnesium halide reagent of formula (II b) in the absence of a catalyst; and, if necessary, isolating a resulting compound of formula (I).

In another aspect, the present invention relates to a process for the manufacture of a compound of formula (I C)

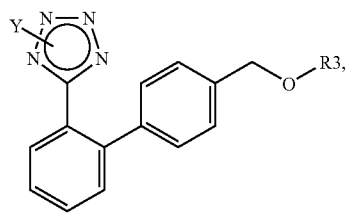

(I C)

wherein Y represents a tetrazole protecting group, and R₃ represents a hydroxyl protecting group; comprising (a') reacting a compound of formula (III a)

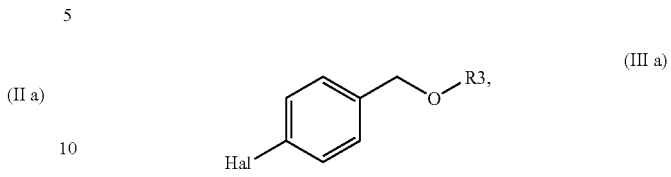

(III a)

wherein Hal is chlorine, bromine or iodine, with an active form of magnesium in an appropriate solvent;

(b') reacting a resulting aryl magnesium halide compound of formula (III b)

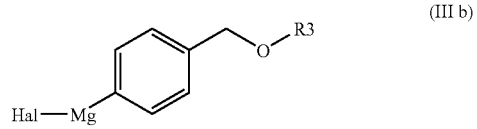

(III b)

in the presence of a transition metal catalyst and a catalytically effective amount of a metal salt additive, with a compound of formula (II c)

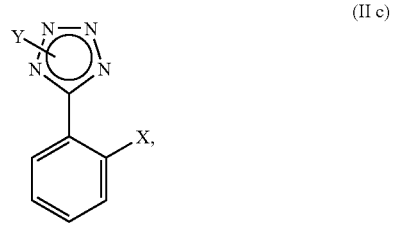

(II c)

wherein X is a substituent which, when bound to a phenyl ring, is not considerably replaceable at room temperature by an aryl magnesium halide reagent of formula (III b) in the absence of a catalyst; and, if necessary, isolating a resulting compound of formula (I C).

A further aspect of the present invention is combining steps (a) and/or (b), or steps (a') and/or (b'), with a subsequent deprotection step (c) resulting in the formation of a compound of formula (I A) or (I B)

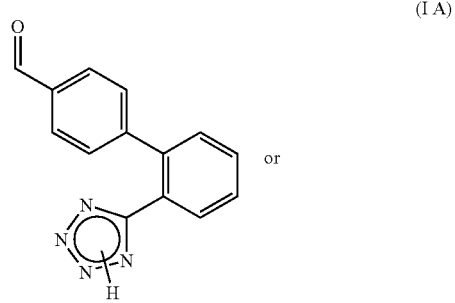

(I A)

or

-continued

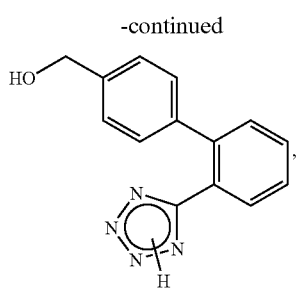

(I B)

respectively.

The resulting compound of formula (I A) or (I B), respectively, is subsequently isolated and may be employed as an intermediate in the preparation of ARBs as referred herein above. It is obvious to those skilled in the art that a compound of formula (I B) may be readily converted to a compound of formula (I A) by treatment with an oxidizing agent according to methods well known in the art.

The reactions described above and below in the variants are carried out, for example, in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° C. to about 140° C., and, if necessary, in a closed vessel, under pressure, in an inert gas atmosphere and/or under anhydrous conditions.

The purpose of introducing protecting groups, e.g., Y and $R_3$, is to protect the functional groups, e.g., tetrazole and a hydroxyl group, respectively, from undesired reactions with reaction components under the conditions used for carrying out the process of the present invention. The choice of protecting groups is known to those skilled in the art and depends on the nature of the functional group to be protected and the reaction conditions.

Well-known protecting groups that meet these conditions and their introduction and removal are described, e.g., in McOmie, "*Protective Groups in Organic Chemistry*", Plenum Press, London, N.Y. (1973); and Greene and Wuts, "*Protective Groups in Organic Synthesis*", John Wiley and Sons, Inc., NY (1999).

A tetrazole protecting group (Y) is, for example, selected from the group consisting of tert-$C_4$-$C_7$-alkyl such as tert-butyl; methyl that is substituted by one, two or three substituents selected from $C_1$-$C_7$-alkyl and $C_1$-$C_7$-alkoxy, for example 1-ethoxyethyl, 1-methoxy-1-methylethyl; 2-tetrahydropyranyl; 2-tetrahydrofuranyl; $C_1$-$C_2$-alkyl that is mono-, di or trisubstituted by phenyl, such as benzyl or benzhydryl or trityl, wherein the phenyl ring is unsubstituted or substituted by one or more, e.g. two or three, substituents e.g.: those selected from the group consisting of tert-$C_1$-$C_7$-alkyl, $C_1$-$C_7$-alkoxy, $C_2$-$C_8$-alkanoyloxy; piperonyl; 1-methyl-1-phenylethyl; fluorenyl; methylthiomethyl; silyl such as tri-$C_1$-$C_4$-alkylsilyl, for example, trimethylsilyl, triethylsilyl or tert-butyl-dimethylsilyl, or di-$C_1$-$C_4$-alkyl-phenylsilyl, for example, dimethyl-phenylsilyl; $C_1$-$C_7$-alkyl-sulphonyl; arylsulphonyl such as phenylsulphonyl wherein the phenyl ring is un-substituted or substituted by one or more, e.g. two or three, substituents e.g. those selected from the group consisting of $C_1$-$C_7$-alkyl, $C_1$-$C_7$-alkoxy, $C_2$-$C_8$-alkanoyl-oxy; $C_2$-$C_8$-alkanoyl such as acetyl or valeroyl; and esterified carboxy such as $C_1$-$C_7$-alkoxy-carbonyl, for example, methoxy-, ethoxy- or tert-butyloxy-carbonyl. Likewise, a tetrazole protecting group (Y) also may be a cation, e.g. of an alkali metal or an earth alkali metal, for example Li(I), Na(I), K(I), Rb(I), Cs(I), Mg(II), Ca(II) and Sr(II).

Examples of preferred protecting groups Y are tert-butyl, benzyl, p-methoxybenzyl, 3,4dimethoxybenzyl, 1-methyl-1-phenylethyl, triphenylmethyl, (p-methoxyphenyl)-diphenyl-methyl, benzyloxymethyl, methoxymethyl, ethoxymethyl, 1-butoxyethyl, 1-ethoxyethyl, 2-tetrahydropyranyl, 2-tetrahydrofuranyl, 1-methoxy-1-methylethyl, 1-methoxycyclohexyl, 1-ethoxycyclohexyl, trimethylsilyl and triethylsilyl.

Particularly preferred protecting groups Y are 1-butoxyethyl, 1-ethoxyethyl, 2-tetrahydropyranyl and 2-tetrahydrofuranyl.

A hydroxyl protecting group ($R_3$) is, for example, selected from the group consisting of tert-$C_4$-$C_7$-alkyl such as tert-butyl; methyl that is substituted by one, two or three substituents selected from $C_1$-$C_7$-alkyl and $C_1$-$C_7$-alkoxy, for example 1-ethoxyethyl, 1-methoxy-1-methylethyl; 2-tetrahydropyranyl; 2-tetrahydrofuranyl; $C_1$-$C_2$-alkyl that is mono-, di or trisubstituted by phenyl, such as benzyl or benzhydryl or trityl, wherein the phenyl ring is unsubstituted or substituted by one or more, e.g. two or three, substituents e.g. those selected from the group consisting of tert-$C_1$-$C_7$-alkyl, $C_1$-$C_7$-alkoxy, $C_2$$C_8$-alkanoyloxy; piperonyl; 1-methyl-1-phenylethyl; fluorenyl; methylthiomethyl; silyl such as tri-$C_1$-$C_4$-alkylsilyl, for example, trimethylsilyl, triethylsilyl or tert-butyl-dimethylsilyl, or di-$C_1$-$C_4$-alkyl-phenylsilyl, for example, dimethyl-phenylsilyl; 2,2-dimethylpropanoyl (i.e. pivaloyl) and esterified carboxy such as tert-butyloxy-carbonyl and benzyloxy-carbonyl.

Examples of preferred protecting groups $R_3$ are 2-tetrahydropyranyl, 2-tetrahydrofuranyl, 1-butoxyethyl and 1-ethoxyethyl.

The general terms used hereinbefore and hereinafter have the following meanings, unless defined otherwise:

$C_1$-$C_1$-Alkyl is, for example, $C_1$-$C_7$-alkyl, such as methyl, ethyl, n-propyl, isopropyl, n-butyl, isobutyl, sec-butyl, tert-butyl or a corresponding pentyl, hexyl or heptyl residue. $C_1$-$C_4$-alkyl, especially methyl or ethyl, is preferred.

$C_2$-$C_{10}$-Alkylene is, for example, $C_2$-$C_6$-alkylene, such as ethylene, propylene, butylene, 1,2-dimethylethylene, 2,2-dimethylpropylene or 1,4dimethyl-1,4-butylene. $C_2$-$C_4$-Alkylene, especially, ethylene or propylene, is preferred.

Hal represents in particular chlorine and bromine.

$C_1$-$C_7$-Alkoxy is, for example, methoxy, ethoxy, n-propyloxy, isopropyloxy, n-butyloxy, iso-butyloxy, sec-butyloxy, tert-butyloxy or a corresponding pentyloxy, hexyloxy, or heptyloxy residue. $C_1$-$C_4$-alkoxy is preferred. Especially preferred is methoxy, ethoxy and butoxy.

$C_2$-$C_8$-Alkanoyl is, for example, $C_2$-$C_5$-alkanoyl such as acetyl, propionyl, butyryl, valeroyl, or pivaloyl. Especially preferred is acetyl.

Steps (a) and (a'):

An active form of magnesium is, for example, magnesium turnings of the type normally used for such transformations, magnesium chips, magnesium powder or magnesium rods.

Furthermore, an active form of magnesium is magnesium that is activated by a catalytic amount of iodine, bromine, 1,2-dibromoethane, a hydride reagent or the arylmagnesium halide reagent intended to be prepared.

A suitable amount of magnesium is 1.0 to 1.8 molar equivalents, preferably 1.0 to 1.2 molar equivalents, with respect to the amount of a compound of formula (II a) or (III a) used.

The reaction is carried out, for example, in a suitable inert solvent or a mixture of solvents. Inert solvents conventionally do not react with the corresponding starting material of formula (II a) or (III a). Appropriate solvents are ethereal solvents, such as ethyl ether, tert-butyl methyl ether, tetrahydrofuran, butyl ether, 1,2-dimethoxyethane or 1,2-diethoxyethane, or a mixture of two or more of these solvents, or a mixture of one of these solvents and an aromatic solvent such as toluene or xylene. A preferred solvent is tetrahydrofuran.

A suitable reaction temperature preferably is between 0° and 75° C., more preferably between 10° and 35° C.

Steps (b) and (b'):

The coupling step (b) or (b') is carried out in the presence of a transition metal catalyst. A suitable transition metal is, for example, nickel, palladium, platinum, cobalt, manganese or copper. A useful transition metal salt is, for example, a nickel (II), a palladium(II), a platinum(II), a cobalt(II), a manganese (II), a copper(I) or a copper(II) salt such as the chloride, bromide, iodide, hydroxide, oxide, acetate, hydroxyacetate, propionate, succinate, trifluoroacetate, acetylacetonate, nitrate, cyanide, sulfate, trifluoromethanesulfonate, methanesulfonate, benzenesulfonate or p-toluenesulfonate thereof.

A suitable transition metal catalyst is preferably a complex of a transition metal or a transition metal salt and one, two or up to four coordinating ligands. The transition metal catalyst may be preformed or it may be generated in situ in the reaction mixture. A suitable transition metal catalyst may also be the uncomplexed transition metal in its elemental form or an uncomplexed transition metal salt. The uncomplexed transition metal or its salt may be supported on carbon, silica, alumina or diatomaceous earth.

Suitable ligands are olefins, such as 1,5-cyclooctadiene; tri($C_2$-$C_4$-alkyl)amines, such as triethylamine and ethyl-di-isopropylamine; N-$C_1$-$C_4$-alkyl-piperidines, such as N-methyl-piperidine; N,N,N',N'-tetramethylethylenediamine; heterocyclic amines and diamines, such as pyridine, N-methylimidazol, 2,2'-dipyridyl, 1,10-phenanthroline, wherein the ring is unsubstituted or substituted by one or more, e.g. two or three, $C_1$-$C_4$-alkyl-residues, as for example in collidine; linear and cyclic ethers containing two or more, e.g. three or four, oxygen atoms, such as 1,2-dimethoxyethane, 1,2-diethoxyethane, di(ethylene glycol) dmethyl ether and 1,2-dimethoxybenzene.

Particularly suitable ligands are those containing one or two trivalent phosphorus atoms, for example, triphenylphosphine, tri(ortho-tolyl)phosphine and tri(para-tolyl)phosphine, tri($C_1$-$C_8$-alkyl)phosphines such as trimethylphosphine, triethylphosphine, tributylphosphine, tri(1,1-dimethylethyl)phosphine, tri($C_4$-$C_7$-cycloalkyl)phosphines such as tricyclopentylphosphine and tricyclohexylphosphine, tri($C_1$-$C_6$-alkyl)phosphites such as trimethylphosphite, triethylphosphite and tri(1-methylethyl)phosphite, tri($C_4$-$C_7$-cycloalkyl)phosphites such as tricyclopentylphosphite and tricyclohexylphosphite, 1,2-bis(diphenylphosphino)ethane (i.e. dppe), 1,3-bis(diphenylphosphino)propane (i.e. dppp), 1,4bis(diphenylphosphino)butane (i.e. dppb), 1,1'-bis(diphenylphosphino)ferrocene (i.e. dppf), 1,1'-bis(di-[2-propyl]-phosphino) ferrocene, 1,1'-bis(di-tert-butyl-phosphino)ferrocene. 1,2-bis(diphenylphosphino)benzene, 2,2'-bis(diphenylphosphino)1,1'-biphenyl (i.e. BIPHEP), 2,2'-bis(diphenylphosphino)-1,1'-binaphtyl (i.e. BINAP), bis(2-diphenylphosphinophenyl)ether (i.e. DPEphos), 9,9-dimethyl-4,5-bis(diphenylphosphino)xanthene (i.e. XANTPHOS).

Transition metal salts are derived from above specific transition metals.

Preferred transition metal salts are nickel(II) chloride, nickel(II) bromide and nickel(II) acetylacetonate. A particularly preferred transition metal salt is nickel(II) chloride.

Preferred ligands are triphenylphosphine, 1,2-bis(diphenylphosphino)ethane (i.e. dppe), 1,3-bis(diphenylphosphino)propane (i.e. dppp), 1,1'-bis(diphenylphosphino)ferrocene (i.e. dppf). A particularly preferred ligand is 1,2-bis(diphenylphosphino)ethane (i.e. dppe).

Preferred catalysts are dichlorobis(triphenylphophine)nickel(II), dichloro[1,2-bis(diphenylphosphino)ethane]nickel(II), dichloro[1,3-bis(diphenylphosphino)propane]-nickel(II). A particularly preferred catalyst is dichloro[1,2bis(diphenylphosphino)ethane]-nickel(II).

The amount of nickel catalyst used is preferably between 0.05 and 2 molar % relative to N-protected tetrazole starting material of formula (II c), preferably between 0.2 and 1.5 molar %.

Likewise preferred transition metal salts are palladium(II) chloride, palladium(II) bromide and palladium(II) acetate. A particularly preferred transition metal salt is palladium(II) chloride.

Preferred ligands are triphenylphosphine, 1,3-bis(diphenylphosphino)propane (i.e. dppp), 1,1'-bis(diphenylphosphino)ferrocene (i.e. dppf). A particularly preferred ligand is 1,1'-bis(diphenylphosphino)ferrocene (i.e. dppf).

Preferred palladium catalysts are dichlorobis(triphenylphophine)palladium(II), dichloro[1,3-bis(diphenylphosphino)propane]palladium(II) and dichloro[1,1'-bis(diphenylphosphino)ferrocene]palladium(II) or its dichloromethane adduct. A particularly preferred palladium catalyst is dichloro[1,1'-bis(diphenylphosphino)ferrocene]palladium(II), or a dichloromethane adduct thereof.

The amount of palladium catalyst used is preferably between 0.01 and 1 molar % relative to N-protected tetrazole starting material (II c), preferably between 0.05 and 0.3 molar %.

The coupling reaction in step (b) or (b') may involve a metal salt additive. The role of the metal salt additive, which is used in catalytic amounts, is to facilitate the coupling reaction. Compared to couplings with aryl-zinc reagents, the use of catalytic amounts of such a metal salt additive results in the formation of less waste. In addition, in the presence of metal salt additive, a higher conversions of starting material (II c) can be achieved. A useful metal salt additive is a copper(I), copper(II), zinc(II), silver(I), cadmium(II), mercury(II), aluminum(II), gallium(III), indium(III), tin(IV), titanium(IV) and zirconium(IV) salt. Examples of such salts are the corresponding chloride, bromide, iodide, carbonate, hydroxide, oxide, $C_1$-$C_7$-alkanoates such as the acetate and propionate, $C_1$-$C_7$-alkoxides such as the methoxide and ethoxide, trifluoroacetate, acetylacetonate, nitrate, cyanide, sulfate, trifluoromethanesulfonate, methanesulfonate, benzenesulfonate or para-toluenesulfonate.

Preferred metal salt additives are zinc(II) salts such as zinc(II) chloride and zinc(II) bromide. A particularly preferred metal salt additive is zinc(II) chloride.

The amount of metal salt additive used is preferably between 0.1 and 8 molar % relative to N-protected tetrazole starting material of formula (II c), preferably between 0.5 and 6 molar %.

Substituent X is a substituent that is not considerably replaceable at room temperature by an arylmagnesium halide reagent of formula (II b) or (III b) in the absence of a transition metal catalyst. In particular, X is, for example, chlorine or bromine. A preferred substituent X is chlorine.

When X is chlorine, the preferred transition metal of the catalyst is nickel.

When X is bromine, the preferred transition metal of the catalyst is palladium.

Independent of the choice of catalyst, the reaction is carried out, for example, in a suitable inert solvent or a mixture of solvents. Inert solvents conventionally do not react with the corresponding starting materials of formulae (II b), (III b) and (II c).

An appropriate solvent for the reaction is an ethereal solvent, such as ethyl ether, tert-butyl methyl ether, tetrahydrofuran, butyl ether, 1,2-dimethoxyethane or 1,2-diethoxyethane; a dipolar aprotic solvent, such as 1-methyl-2-pyrrolidinone (i.e. NMP) and 1,3-dimethyl-3,4,5,6-tetrahydro-2(1H)-pyrimidinone (i.e. DMPU); an aromatic solvent such as toluene or xylene; or a mixture of two or more solvents selected from the above groups. A preferred solvent is tetrahydrofuran.

The reaction is preferably carried out at a temperature between −10° and 60° C., preferably between 10° and 35° C.

As described herein above, the present inventions provides a process for the preparation of a protected 2'-(1H-tetrazol-5-yl)-biphenyl-4-carbaldehyde of formula (I) as exemplified by the following reaction scheme

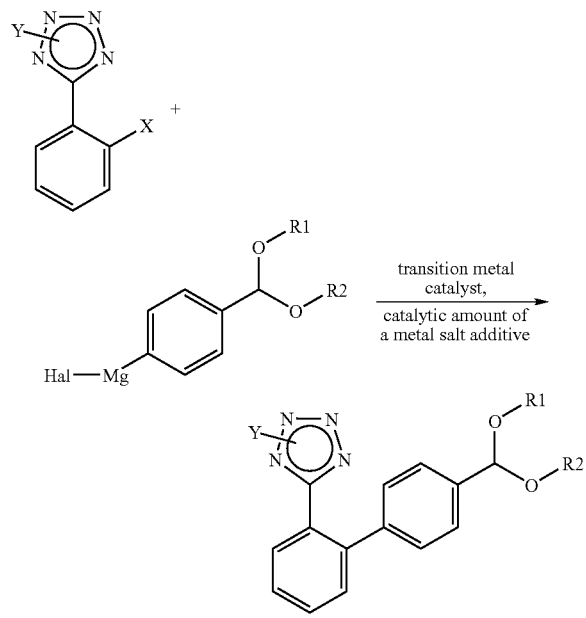

comprising coupling of a N-protected phenyltetrazole (X=Cl or Br; Y=a tetrazole protecting group) with an arylmagnesium halide (Hal=Cl, Br, I; $R_1$, $R_2$=$C_1$-$C_{10}$-alkyl or combined $C_2$-$C_{10}$-alkylene) in the presence of a transition metal catalyst, which is complexed, uncomplexed or supported nickel, palladium, platinum, cobalt, manganese or copper metal or a corresponding salt thereof, and optionally a catalytic amount of a metal salt additive, such as a copper(I), copper(II), zinc (II), silver(I), cadmium(II), mercury(II), aluminum(III), gallium(III), indium(III), tin(IV), titanium(IV) or zirconium(IV) salt, in the presence of an inert solvent or a mixture of inert solvents.

Similarly, the present invention provides a process for the manufacture of a protected alcohol of formula (I C) as exemplified by the reaction scheme below

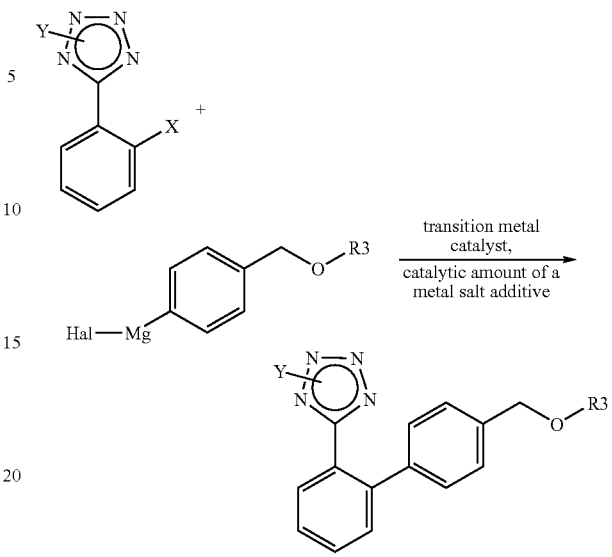

comprising coupling of a N-protected phenyltetrazole (X=Cl or Br; Y=a tetrazole protecting group) with an arylmagnesium halide (Hal=Cl, Br, I; $R_3$=a hydroxyl protecting group) in the presence of a transition metal catalyst, which is complexed, uncomplexed or supported nickel, palladium, platinum, cobalt, manganese or copper metal or a corresponding salt thereof, and optionally a catalytic amount of a metal salt additive, such as a copper(I), copper(II), zinc(II), silver(I), cadmium(II), mercury(II), aluminum(III), gallium(III), indium(III), tin(IV), titanium(IV) or zirconium(IV) salt, in the presence of an inert solvent or a mixture of inert solvents.

Preferred Hal is, for example, Br.

Preferred $R_1$ and $R_2$ are, for example, methyl.

Preferred $R_3$ is, for example, 2-tetrahydropyranyl.

Preferred X is, for example, Cl.

When X is chlorine, a preferred transition metal catalyst is a nickel(O) or nickel(II) complex, for example, a complex of a nickel(II) salt which is coordinated by at least one organo phosphorus compound containing trivalent phosphorus. Nickel(II) complexes comprising two organophosphorus ligands are preferred. Nickel(II) complexes with organophosphorus ligands which contain two trivalent phosphorus atoms; such as dichloro[1,2-bis(diphenylphosphino)ethane] nickel(II) (i.e. $NiCl_2$(dppe)), are particulary preferred. A preferred metal salt additive is, for example, a zinc(II) salt such as $ZnCl_2$ and $ZnBr_2$. Preferred solvents are ethereal solvents, particularly tetrahydrofuran.

When X is chlorine, compounds of formula (I) may be prepared without the metal salt additive (e.g. $ZnCl_2$) in above process, i.e. catalyzing the coupling reaction solely by the nickel catalyst.

When X is bromine, a preferred transition metal catalyst is a palladium complex, for example, a complex of palladium (O) or a complex of a palladium(II) salt with at least one organophosphorus compound containing trivalent phosphorus. Palladium(II) complexes comprising two organophosphorus ligands are preferred. Palladium(II) complexes with organophosphorus ligands which contain two trivalent phosphorus atoms, such as dichloro[1,1'-bis(diphenylphosphino) ferrocene]palladium(II) (i.e. $PdCl_2$(dppf)) or its dichloromethane adduct, are particularly preferred.

A preferred metal salt additive is, for example, a zinc(II) salt such as $ZnCl_2$ and $ZnBr_2$.

In a variation of the present invention, another embodiment of the present invention is a process for the manufacture of a compound of formula (I)

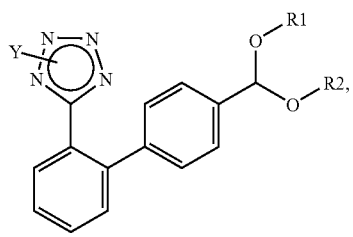

(I)

wherein Y represents a tetrazole protecting group, and $R_1$ and $R_2$, independently of one another, represent $C_1$-$C_{10}$-alkyl, or $R_1$ and $R_2$ combined together form $C_2$-$C_{10}$-alkylene; comprising (a) reacting a compound of formula (II a)

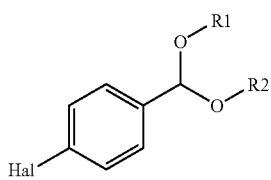

(II a)

wherein Hal is chlorine, bromine or iodine, with an active form of magnesium in an appropriate solvent (b) reacting a resulting aryl magnesium halide compound of formula (II b)

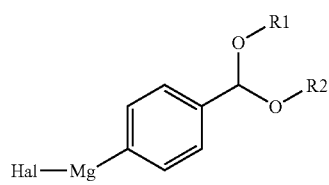

(II b)

in the presence of a transition metal catalyst with a compound of formula (II c)

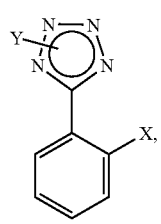

(II c)

wherein X is chlorine, in the absence of a metal salt additive; and, if necessary, isolating a resulting compound of formula (I).

Yet another variation of the present invention is a process for the manufacture of a compound of formula (I C)

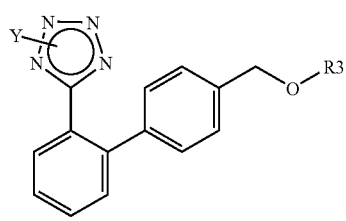

(I C)

wherein Y represents a tetrazole protecting group, and $R_3$ represents a hydroxyl protecting group; comprising (a') reacting a compound of formula (III a)

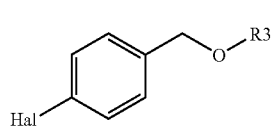

(III a)

wherein Hal is chlorine, bromine or iodine, with an active form of magnesium in an appropriate solvent;

(b') reacting a resulting aryl magnesium halide compound of formula (III b)

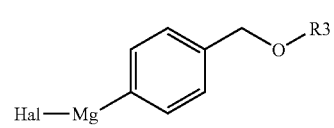

(III b)

in the presence of a transition metal catalyst with a compound of formula (II c)

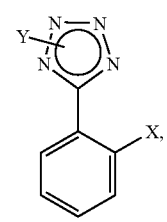

(II c)

wherein X is chlorine, in the absence of a metal salt additive; and, if necessary, isolating a resulting compound of formula (I C).

A further embodiment of the present invention is the reaction step (b) or (b'), respectively, i.e., the specific reaction of a compound of formula (II b) or (III b), respectively, with a compound of formula (II c), wherein X is chlorine. In the instant reaction, surprisingly, no addition of a catalytically effective amount of a metal salt additive is necessary to result in a compound of formula (I) or (I C), respectively.

In the case in which both the transition metal salt and the metal salt additive are omitted, no significant amount of compound of formula (I) or (I C), respectively, is formed from a starting material of formula (II c), wherein X is chlorine.

Isolation Step:

The isolation of a compound of formula (I) or (I C) is carried out according to conventional isolation methods, such as by crystallizing the resulting compound of formula (I) or (I C) from the reaction mixture, if desired or necessary after work-up, especially by extraction, or by chromatography of the reaction mixture, or any combined methods.

Step (c):

For this purpose, the protecting groups of a resulting compound of formula (I) or (I C) of step (b) or (b'), respectively, are removed sequentially or in a single step under conditions of hydrolysis, preferably in the presence of a Bronsted acid.

Step (c) is carried out, for example, by dissolving a compound of formula (I) or (I C) in water or a mixture of water and an appropriate organic solvent and subsequently treating with an acid, preferably, at an elevated temperature.

Appropriate organic solvents are ethers, such as tetrahydrofuran, 1,4-dioxan, butyl ether, nitriles, such as acetonitrile, alcohols, such as methanol, ethanol, 1-propanol, 2-propanol, 1-butanol, isopropyl acetate, toluene, xylene, acetic acid or formic acid. Preferred solvents are methanol and ethanol.

Suitable acids are Bronsted acids, such as sulfuric acid, hydrochloric acid, phosphoric acid, methanesulfonic acid, ethanesulfonic acid, para-toluenesulfonic acid, benzoic acid, acetic acid, formic acid as well as polymer supported Bronsted acids (e.g. acidic ion exchange resins). Preferred acids are sulfuric acid and hydrochloric acid.

The amount of acid used is preferably between 0.05 and 2.0 equivalents with respect to a compound of formula (I) or (I C), more preferably between 0.1 and 1.2 equivalents.

The reaction is carried out at a temperature between 0° C. and the boiling point of the solvent, preferably between 25° and 70° C.

The isolation of a resulting compound of formula (I A) or (I B) is carried out according to conventional isolation methods, such as by crystallizing a compound of formula (I A) or (I B) from the reaction mixture and, if desired or necessary after work-up, especially by extraction, or by chromatography of the reaction mixture or any combined methods thereof. For example, crystallization of the product is accomplished by distilling off all or a part of the organic solvent, adding water, cooling the mixture or a combination of these measures.

Several starting materials of formulae (II a) and (III a) are known in the art and can be prepared according to methods well known in the art For example, a compound of formula (II a) may be obtained by conventional acid catalyzed acetalization of a 4-halobenzaldehyde in the presence of an alcohol or diol. For example, the preparation of compound of formula (II a) with Hal being bromine, and $R_1$ and $R_2$ being methyl, is described in Journal of Organic Chemistry 1991, 56, 4280. The corresponding compound with $R_1$ and $R_2$ being ethyl can be prepared in ethanol in the presence of triethyl orthoformate and an acid catalyst. A compound of formula (III a) may be prepared, for example, by conventional acid catalyzed reaction of a 4-halobenzylalcohol with a suitable alkylating agent such as 3,4-dihydro-2H-pyran. For example, the preparation of compound of formula (III a) wherein Hal is bromine, and $R_3$ is tetrahydropyran-2-yl, is described in Tetrahedron 1983, 39, 2531.

Several starting materials of formula (II c) with different protecting groups Y are known in the art. The preparation of some examples is described in EP 788487.

The following examples illustrate the invention described above; however, they are not intended to limit its extent in any manner, for example, to specific reaction conditions.

EXAMPLE 1

Preparation of 5-(4'-[1,3]dioxan-2-yl-biphenyl-2-yl)-2-(1-methyl-1-phenyl-ethyl)-2H-tetrazole

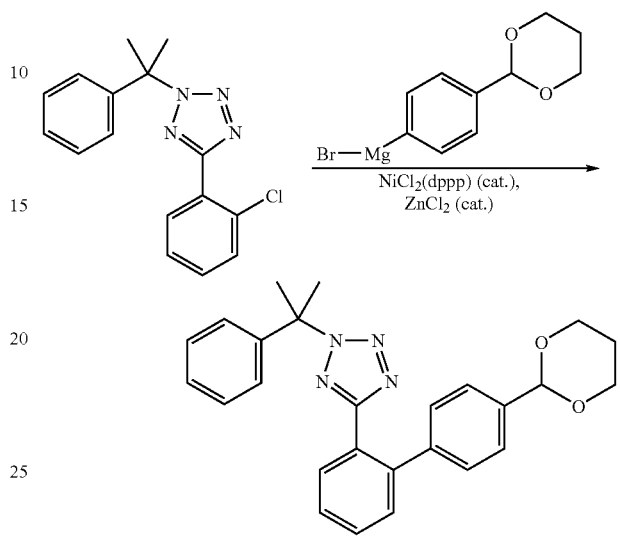

To magnesium turnings (0.882 g) are added under anhydrous conditions 12 mL of a solution of 2-(4-bromo-phenyl)-[1,3]dioxane (8.02 g; 33 mmol) in anhydrous tetrahydrofuran (33 mL). The mixture is warmed to about 50° C., and five drops of 1,2-dibromoethane are added. After the reaction starts, the mixture is heated to reflux and the remainder of the solution of 2-(4-bromo-phenyl)-[1,3]dioxane is added over 40 minutes. The resulting mixture is further stirred at 60° C. for one hour and finally allowed to cool down to room temperature. The concentration of 4-[1,3]dioxan-2-yl)phenyl-magnesium bromide in the solution above the excess of magnesium turnings is 0.50 M according to titration.

In another flask, dichloro[1,3-bis(diphenylphosphino)propane]nickel(II) (0.022 g; 0.04 mmol) is suspended in tert-butyl methyl ether (3 mL) and cooled to about 0° C. before a 0.5 M solution of zinc chloride in tetrahydrofuran (0.40 mL; 0.20 mmol) and a solution of 5-(2-chloro-phenyl)-2-(1-methyl-1-phenyl-ethyl )-2H-tetrazole (1.20 g; 4.0 mmol) in tert-butyl methyl ether (1.2 mL) are added. To the vigorously stirred resulting suspension is added at about 0° C. 9.6 mL of the above 0.5 M 4-([1,3]dioxan-2-yl)phenylmagnesium bromide solution (4.8 mmol) over one hour. The resulting dark brown solution is allowed to warm up and further stirred at room temperature for 20 hours. The mixture is cooled to about 0° C., quenched with 10 mL of a 3.8% solution of ammonium chloride in water and diluted with ethyl acetate (25 mL). The aqueous phase is separated and extracted with ethyl acetate (25 mL). The combined organic phases are washed with a 0.5 M solution of sodium hydroxide in water (10 mL) and with a 10% solution of sodium chloride in water (10 mL). The combined organic phases are evaporated in vacuo. A solution of the resulting pale green solid in a small amount of ethyl acetate is filtered and evaporated. The resulting pale green solid is purified by column chromatography on silica gel eluting with a 1:10 mixture of tert-butyl methyl ether and toluene to afford 5-(4'-[1,3]dioxan-2-yl-biphenyl-2-yl)-2-(1-methyl-1-phenyl-ethyl)-2H-tetrazole as colorless crystals.

¹H-NMR (400 MHz, d₆-DMSO): 1.47-1.52 (m, 1H), 2.01 (s, 6H), 2.02-2.07 (m, 1H), 3.96-4.02 (m, 2H), 4.17-4.21 (m, 2H), 5.55 (s, 1H), 6.95-6.98 (m, 2H), 7.10-7.13 (m, 2H), 7.32-7.39 (m, 5H), 7.51-7.53 (m, 1H), 7.56-7.61 (m, 1H), 7.65-7.69 (m, 1H), 7.78-7.80 (m, 1H). Melting range: 102-106° C.

EXAMPLE 2

Preparation of 5-(4'-diethoxymethyl-biphenyl-2-yl)-2-(tetrahydro-pyran-2-yl)-2H-tetrazole

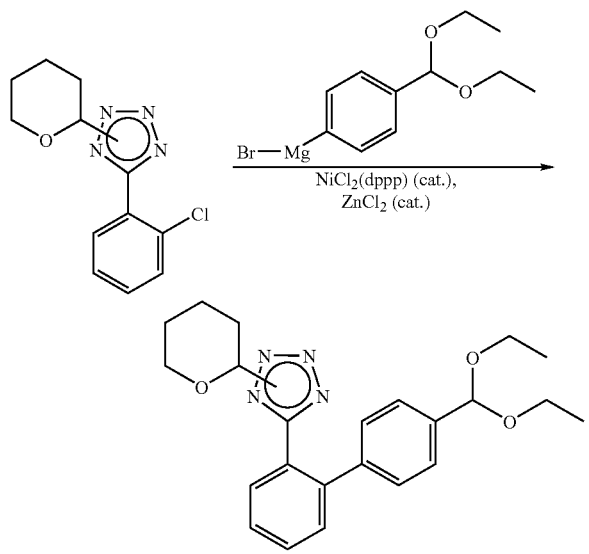

To magnesium turnings (2.92 g) is added under anhydrous conditions one fifth of a solution of 1-bromo-4-(diethoxymethyl)benzene (25.9 g; 100 mmol) in anhydrous tetrahydrofuran (80 mL). The mixture is warmed to about 40° C. and 1,2-dibromoethane (0.09 mL; 1.0 mmol) is added. After the reaction starts, the remainder of the solution of 1-bromo-4-(diethoxymethyl)benzene is added over one hour. The resulting mixture is further stirred at 40° C. for two hours and at room temperature for 30 minutes and is finally diluted by adding anhydrous tetrahydrofuran (25 mL). The concentration of 4-(diethoxymethyl)phenyl-magnesium bromide in the solution above the excess of magnesium turnings is 0.46 M according to titration.

In another flask, dichloro[1,3bis(diphenylphosphino)propane]nickel(II) (0.027 g; 0.05 mmol) is suspended in tert-butyl methyl ether (3.8 mL) and cooled to about 0° C. before a 0.5 M solution of zinc chloride in tetrahydrofuran (0.50 mL; 0.25 mmol) and a solution of a mixture of 5-(2-chlorophenyl)-2-(tetrahydropyran-2-yl)-2H-tetrazole and 5-(2-chlorophenyl)-1-(tetrahydropyran-2-yl)-1H-tetrazole (1.32 g; 5.0 mmol) in tert-butyl methyl ether (1.3 mL) are added. To the vigorously stirred resulting suspension is added at about 0° C. 13 mL of the above 0.46 M 4-(diethoxymethyl)phenylmagnesium bromide solution (6.0 mmol) over one hour. The resulting black-yellow solution is stirred at about 0° C. for 5 hours, allowed to warm up and further stirred at room temperature for 19 hours. The mixture is cooled to about 0° C. and quenched with a 7.5% solution of ammonium chloride in water (10 mL). The aqueous phase is separated and extracted with ethyl acetate (25 mL). The combined organic phases are washed with water (10 mL), a 7.5% solution of sodium carbonate in water (10 mL) and a 10% solution of sodium chloride in water (10 mL). The combined organic phases are evaporated in vacuo. A solution of the resulting brown-yellow oil in a small amount of ethyl acetate is filtered and evaporated. The resulting oil (2.68 g) is purified by column chromatography on silica gel eluting with a 1:4 mixture of ethyl acetate and hexane (in the presence of 0.2 volume-% of triethylamine) to afford the main isomer (N2-isomer) 5-(4'-diethoxymethyl-biphenyl-2-yl)-2-(tetrahydro-pyran-2-yl)-2H-tetrazole as a colorless oil.

¹H-NMR of N2-isomer (400 MHz, CDCl₃): 1.24 (t, J=7.2 Hz, 6H), 1.60-1.67 (m, 3H), 1.86-2.03 (m, 2H), 2.11-2.17 (m, 1H), 3.50-3.73 (m, 6H), 5.49 (s, 1H), 5.97-5.99 (m, 1H), 7.17-7.20 (m, 2H), 7.37-7.39 (m, 2H), 7.43-7.56 (m, 3H), 7.90-7.92 (m, 1H).

EXAMPLE 3

Preparation of 5-(4'-[1,3]dioxan-2-yl-biphenyl-2-yl)-2-(tetrahydro-pyran-2-yl)-2H-tetrazole and 5-(4'-[1,3]dioxan-2-yl-biphenyl-2-yl)-1-(tetrahydro-pyran-2-yl)-1H-tetrazole

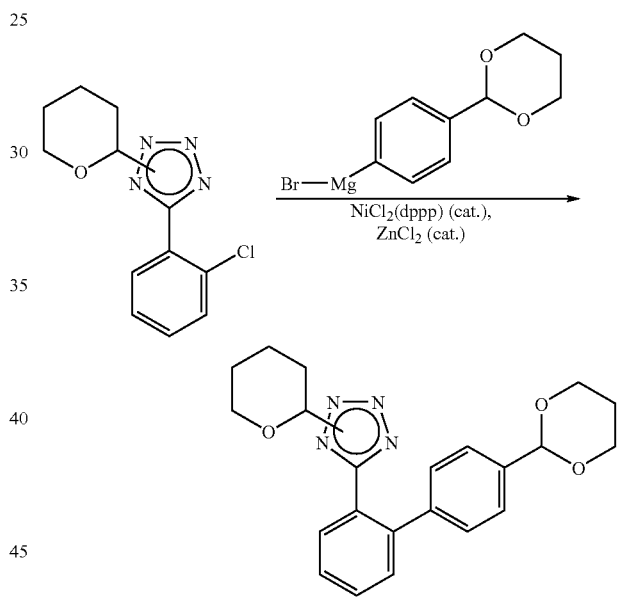

A suspension of magnesium turnings (2.68 g) in anhydrous tetrahydrofuran (20 mL) is cooled to 10° C. and five drops of 1,2-dibromoethane are added. 2 mL of a solution of 2-(4-bromo-phenyl)-[1,3]dioxane (24.3 g; 100 mmol) in anhydrous tetrahydrofuran (80 mL) is added at 10° C. under vigorous stirring. After the reaction starts the remainder of the solution of 2-(4-bromo-phenyl)-[1,3]dioxane is added over 90 minutes. The resulting mixture is further stirred at about 16° C. for 2 hours and at 25° C. for 75 minutes. The concentration of 4-([1,3]dioxan-2-yl)phenylmagnesium bromide in the solution above the excess of magnesium turnings is about 0.90 M. In another flask, dichloro[1,3-bis(diphenylphosphino)propane]nickel(II) (0.054 g; 0.10 mmol) is suspended in 1,2-dimethoxyethane (7.7 mL) and cooled to about 0° C. before a 0.5 M solution of zinc chloride in tetrahydrofuran (1.0 mL; 0.50 mmol) and a solution of a mixture of 5-(2-chlorophenyl)-2-(tetrahydropyran-2-yl)-2H-tetrazole and 5-(2-chlorophenyl)-1-(tetrahydropyran-2-yl)-1H-tetrazole (2.65 g; 10.0 mmol) in 1,2-dimethoxyethane (2.7 mL) are added. To the vigorously stirred resulting suspension is added at about 0° C. 13.4 mL of the above 0.90 M 4-([1,3]dioxan-2-yl)phenylmagnesium bromide solution (12.0 mmol) over one hour. The resulting brown-yellow solution is allowed to warm up and further stirred at room temperature for 3 hours. The mixture is cooled to about 0° C. and quenched with a 7.5% solution of ammonium chloride in water (20 mL). The aqueous phase is separated and extracted with ethyl acetate (50 mL). The combined organic phases are washed with water (20 mL), a 7.5 % solution of sodium carbonate in water (20 mL) and water (20 mL). The combined organic phases are evaporated in vacuo. A solution of the resulting oil in a small amount of ethyl acetate is filtered and evaporated. The resulting oil is purified by column chromatography on silica gel eluting with a 1:2 mixture of ethyl acetate and hexane to afford the main isomer (N2-isomer) 5-(4'-[1,3]dioxan-2-yl-biphenyl-2-yl2-(tetrahydro-pyran-2-yl)-2H-tetrazole as a colorless oil and the minor isomer (N1-isomer) 5-(4'-[1,3]dioxan-2-yl-biphenyl-2-yl)-1-(tetrahydro-pyran-2-yl)-1H-tetrazole as colorless crystals.

$^1$H-NMR of N2-isomer (400 MHz, CDCl$_3$): 1.42-1.47 (m, 1H), 1.57-1.65 (m, 3H), 1.79-1.87 (m, 1H), 1.96-2.03 (m, 1H), 2.10-2.27 (m, 2H), 3.60-3.69 (m, 2H), 3.95-4.01 (m, 2H), 4.23-4.27 (m, 2H), 5.48 (s, 1H), 5.98-6.00 (m, 1H), 7.18-7.21 (m, 2H), 7.38-7.42 (m, 3H), 7.46-7.54 (m, 2H), 7.89-7.91 (m, 1H). $^1$H-NMR of N1-isomer (400 MHz, CDCl$_3$): 0.98-1.02 (m, 1H), 1.31-1.36 (m, 1H), 1.42-1.47 (m, 2H), 1.51-1.61 (m, 1H), 1.87-1.96 (m, 2H), 2.14-2.26 (m, 1H), 3.25-3.31 (m, 1H), 3.70-3.75 (m, 1H), 3.93-4.00 (m, 2H), 4.22-4.27 (m, 2H), 4.84-4.87 (m, 1H), 5.45 (s, 1H), 7.12-7.15 (m, 2H), 7.40-7.42 (m, 2H), 7.50-7.68 (m, 4H). Melting range of N1-isomer 125-127° C.

EXAMPLE 4

Preparation of 2'-(1H-tetrazol-5-Yl)biphenyl-4-carbaldehyde

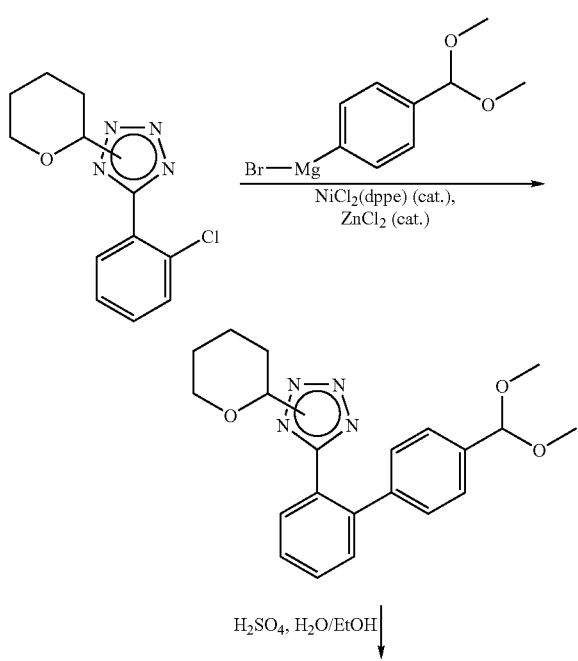

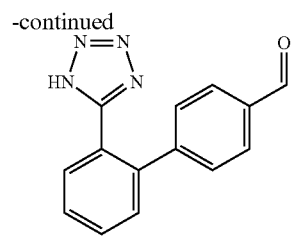

A suspension of magnesium turnings (6.31 g) in anhydrous tetrahydrofuran (59 mL) is cooled to 14° C., treated with a 1 M solution of diisobutylaluminum hydride in tetrahydrofuran (2.35 mL, 2.4 mmol) and stirred for 20 min. At 14° C., 1-bromo-4-dimethoxymethyl-benzene (2.72 g; 11.7 mmol) is added under vigorous stirring. After the reaction starts, more 1-bromo-4-dimethoxymethyl-benzene (51.79 g; 223 mmol) is added over 45 minutes, while the mixture is diluted with two portions of anhydrous tetrahydrofuran (59 mL each). The resulting mixture is further stirred at about 25° C. for 2.5 hours. The concentration of 4-(dimethoxymethyl)phenyl-magnesium bromide in the solution above the excess of magnesium turnings is about 1.0 M. In another flask, a mixture of 5-(2-chlorophenyl)-2-(tetrahydropyran-2-yl)-2H-tetrazole and 5-(2-chlorophenyl)-1-(tetrahydropyran-2-yl)-1H-tetrazole (98.2% content; 53.91 g; 200 mmol) is dissolved in anhydrous tetrahydrofuran (37 mL) under an inert atmosphere and dichloro[1,2-bis(diphenylphosphino)ethane]nickel(II) (0.862 g; 1.60 mmol) and a 0.5 M solution of zinc chloride in tetrahydrofuran (6.0 mL; 3.0 mmol) are added. The vigorously stirred resulting suspension is cooled to about 14° C .and the above 1.0 M 4-(dimethoxymethyl)phenylmagnesium bromide solution (229 mL; 230 mmol) is added over one hour while keeping the temperature below 25° C. by external cooling. The dark brown reaction mixture is stirred at room temperature for 17.5 hours. After that, more than 99% of the starting material is converted, and methanol (8.0 mL) is added to the mixture.

A part of the solvents (about 156 mL) are distilled off under reduced pressure. Ethanol (307 mL in total) is added while more solvents are distilled off. To the resulting brown mixture is added at 50° C. over 10 minutes a mixture of a 2 M aqueous sulfuric acid solution (32 mL; 64 mmol) and water (75 mL). The mixture is further stirred at 50° C. for 50 minutes, at 60° C. for 1.5 hours and at 35° C. overnight. The mixture is stirred at 60° C. with activated carbon (5.3 g) and filter aid (2.7 g) for 40 minutes in total and is then filtered at about 550C. The orange filtrate is concentrated by distilling off about 202 mL of solvents under reduced pressure. After adding water (48 mL) at 50° C., the stirred resulting suspension is allowed to cool to room temperature overnight and is further stirred at about 10° C. for 90 minutes. The solids are collected by filtration, washed with a 1:2 mixture of ethanol and water and water and are dried under reduced pressure at about 60° C. to afford 2'-(1H-tetrazol-5-yl)biphenyl-4-carbaldehyde as pale yellow, crystalline solid.

Melting range: 188.6-189.9° C.

EXAMPLE 5

Preparation of 5-(4'-diethoxymethyl-biphenyl-2-yl)-2-(tetrahydro-pyran-2-yl)-2H-tetrazole

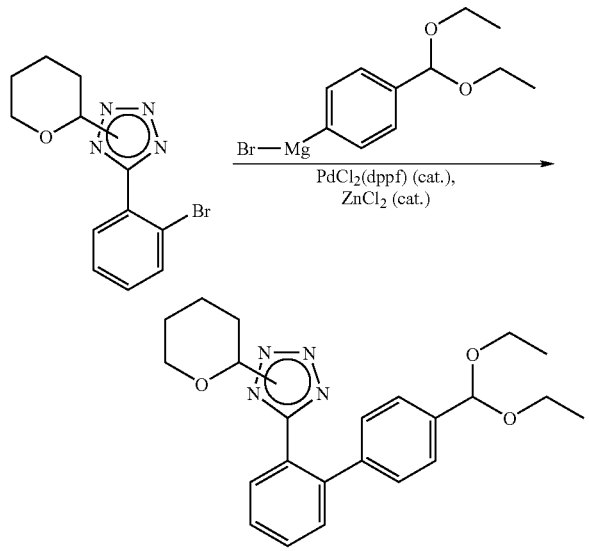

To a suspension of magnesium turnings (5.11 g) in anhydrous tetrahydrofuran (40 mL) is added 1,2-dibromoethane (0.106 mL; 1.2 mmol). The suspension is cooled to 12° C. and 6 mL of a solution of 1-bromo-4-(diethoxymethyl)benzene (53.6 g; 200 mmol) in anhydrous tetrahydrofuran (120 mL) and a second portion of 1,2-dibromoethane (0.106 mL; 1.2 mmol) are added. After the reaction starts the remainder of the solution of 1-bromo-4-(diethoxymethyl)benzene is added over 90 minutes. The resulting mixture is further stirred at 20 to 25° C. for 2.5 hours. The mixture is diluted with anhydrous tetrahydrofuran to a total volume of 250 mL. The concentration of 4-(diethoxymethyl)phenylmagnesium bromide in the solution above the excess of magnesium turnings is about 0.78 M. In another flask are added to dichloro[1,1'-bis(diphenylphosphino)ferrocene]palladium(II) dichloromethane adduct (0.012 g; 0.015 mmol) a 0.5 M zinc chloride solution in tetrahydrofuran (0.6 mL; 0.30 mmol) and a solution of a mixture of 5-(2-bromophenyl)-2-(tetrahydropyran-2-yl)-2H-tetrazole and 5-(2-bromophenyl)-1-(tetrahydropyran-2-yl)-1H-tetrazole (4.99 g; 14.3 mmol) in tetrahydrofuran (30 mL). To the stirred resulting yellow-orange solution is added at room temperature 22.2 mL of the above 0.78 M 4-(diethoxymethyl)phenylmagnesium bromide solution (17.3 mmol) over two hours. The resulting orange solution is further stirred at room temperature for 18 hours. After that, no more starting material could be detected by thin layer chromatography. The mixture is cooled to about 0° C. and a solution of sodium hydrogencarbonate (2.0 g) in water (25 mL) and ethyl acetate (30 mL) are added. The aqueous phase is separated and extracted with ethyl acetate (40 mL). The combined organic phases are washed with a solution of sodium hydrogencarbonate (2.0 g) in water (25 mL) and twice with water (25 mL) before they are evaporated in vacuo. The resulting orange oil is purified by column chromatography on silica gel eluting with a 1:4 mixture of ethyl acetate and hexane (in the presence of 0.3 volume-% of triethylamine) to afford the main isomer (N2-isomer) 5-(4'-diethoxymethyl-biphenyl-2-yl)-2-(tetrahydro-pyran-2-yl)-2H-tetrazole as a pale yellow oil.

$^1$H-NMR of N2-isomer (400 MHz, CDCl$_3$): 1.24 (t, J=7.2 Hz, 6H), 1.59-1.67 (m, 3H), 1.85-2.03 (m, 2H), 2.11-2.18 (m, 1H), 3.50-3.74 (m, 6H), 5.49 (s, 1H), 5.97-5.99 (m, 1H), 7.17-7.20 (m, 2H), 7.38-7.40 (m, 2H), 7.43-7.56 (m, 3H), 7.90-7.92 (m, 1H).

EXAMPLE 6

Preparation of 2'-(1H-tetrazol-5-yl)-biphenyl-4-carbaldehyde

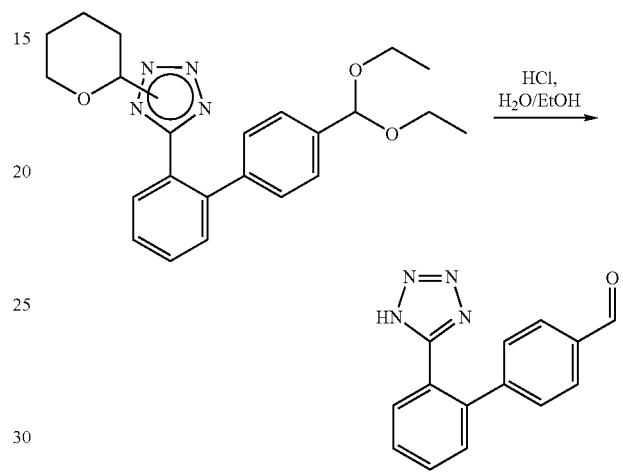

To 5-(4'-diethoxymethyl-biphenyl-2-yl)-2-(tetrahydropyran-2-yl)-2H-tetrazole (0.408 g; 1.00 mmol) are added 94% ethanol (2.5 mL) and a 2N aqueous solution of hydrochloric acid (0.5 mL; 1.0 mmol). The resulting solution is heated to 45° C. for 3 hours. After the addition of water (about 2 mL) the mixture is allowed to cool down to room temperature and then stirred at 0 to 5° C. for 30 minutes. The resulting suspension is filtered and the solids are washed with a small amount of water, dried in vacuo at 40° C. to afford 2'-(1H-tetrazol-5-yl)biphenyl-4-carbaldehyde as white, crystalline powder.

Melting point: 187.5-190.0° C.

EXAMPLE 7

Preparation of 5-(4'-dimethoxymethyl-biphenyl-2-yl)-2-(tetrahydro-pyran-2-yl)-2H-tetrazole in the Presence of a Nickel Catalyst and in the Absence of a Zinc Salt

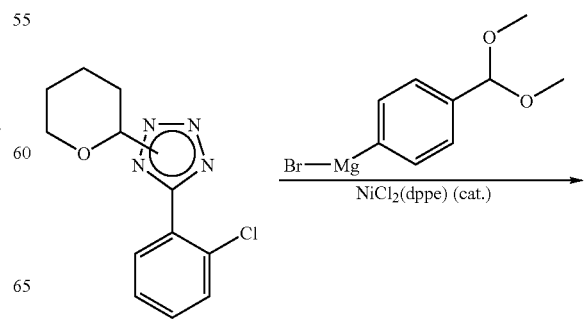

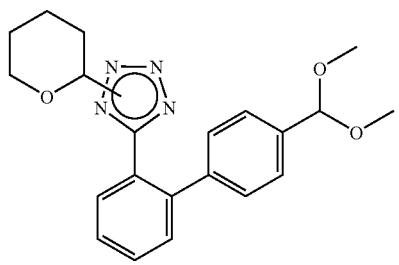

A suspension of magnesium turnings (2.35 g) in anhydrous tetrahydrofuran (66 mL) is cooled to 14° C., treated with a 1 M solution of diisobutylaluminium hydride in tetrahydrofuran (1.8 mL; 1.8 mmol) and stirred for 20 min. At 14° C., 1-bromo-4-dimethoxymethyl-benzene (1.02 g; 4.4 mmol) is added under vigorous stirring. After the reaction starts, more 1-bromo-4-dimethoxymethyl-benzene (19.32 g; 83.6 mmol) is added over 50 minutes. The resulting mixture is further stirred at about 25° C. for 2.5 hours. The concentration of 4-(dimethoxymethyl)phenylmagnesium bromide in the solution above the excess of magnesium turnings is about 0.96 M. In another flask, a mixture of 5-(2-chlorophenyl)-2-(tetrahydropyran-2-yl)-2H-tetrazole and 5-(2-chlorophenyl)-1-(tetrahydropyran-2-yl)-1H-tetrazole (94% content; 4.22 g; 15.0 mmol) is dissolved in anhydrous tetrahydrofuran (2.8 mL) under an inert atmosphere and dichloro[1,2-bis(diphenylphosphino)ethane]nickel(II) (80.8 mg; 0.15 mmol) is added. The vigorously stirred resulting suspension is cooled to about 15° C. and the above 0.96 M 4-(dimethoxymethyl)phenylmagnesium bromide solution (18 mL; 17.3 mmol) is added over one hour while keeping the temperature below 25° C. by external cooling. The dark brown reaction mixture is agitated at room temperature for 22.5 hours. After that, about 94% of the starting material are converted. Methanol (1.2 mL; 30 mmol) is added to the mixture followed by isopropyl acetate (35 mL), a solution of ammonium chloride (0.4 g) in water (10 mL) and water (10 mL). The layers are separated. The organic layer is washed with water (10 mL), three times with a solution of sodium hydrogencarbonate (1.0 g) in water (12 mL) and twice with water (10 mL) before it is evaporated in vacuo. The resulting brown oil is purified by column chromatography on silica gel eluting with a 1:4 mixture of ethyl acetate and hexane (in the presence of 0.3 volume-% of triethylamine) to afford the main isomer (N2-isomer) 5-(4'-dimethoxymethyl-biphenyl-2-yl)-2-(tetrahydro-pyran-2-yl) 2H-tetrazole as a pale yellow oil.

$^1$H-NMR of N2-isomer (400 MHz, CDCl$_3$): 1.59-1.68 (m, 3H), 1.86-1.93 (m, 1H), 1.96-2.04 (m, 1H), 2.12-2.20 (m, 1H), 3.34 (s, 6H), 3.65-3.76 (m, 2H), 5.38 (s, 1H), 5.95-5.98 (m, 1H), 7.18-7.21 (m, 2H), 7.36-7.38 (m, 2H), 7.447.56 (m, 3H), 7.90-7.92 (m, 1H).

EXAMPLE 8

Attempt for the Preparation of 5-(4'-dimethoxymethyl-biphenyl-2-yl)-2-(tetrahydro-pyran-2-yl)-2H-tetrazole in the Absence of a Catalyst

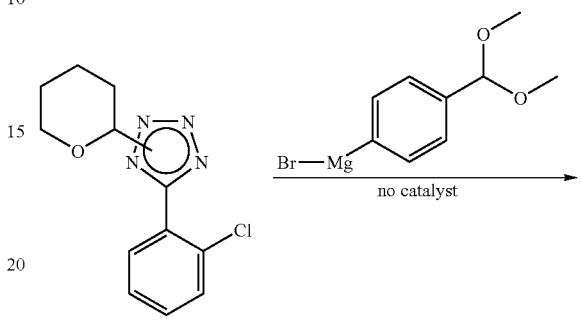

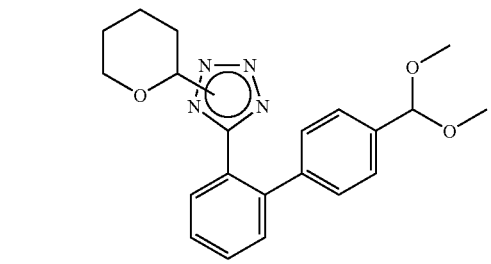

A mixture of 5-(2-chlorophenyl)-2-(tetrahydropyran-2-yl)-2H-tetrazole and 5-(2-chlorophenyl) 1-(tetrahydropyran-2-yl)-1H-tetrazole (94% content; 4.22 g; 15.0 mmol; same batch as used in Example 7) is dissolved in anhydrous tetrahydrofuran (2.8 mL) under an inert atmosphere. The vigorously stirred resulting suspension is cooled to about 15° C. and a 0.96 M 4-(dimethoxymethyl)phenylmagnesium bromide solution (18 mL; 17.3 mmol; same batch as used in Example 7) is added over one hour while keeping the temperature below 25° C. by external cooling. The brown reaction mixture is agitated at room temperature for 22 hours. After that, HPLC analysis is done on a sample which is, as usual, hydrolyzed with dilute aqueous hydrochloric acid. The analysis shows mainly unconverted starting material (detected as 5-(2-chlorophenyl)-1H-tetrazole) and less than 0.25 area % of C—C-coupling product (detected as 2'-(1H-tetrazol-5-yl)biphenyl-4-carbaldehyde). Finally, when methanol (1.2 mL; 30 mmol) is added to the mixture, an unusually strong exotherm is observed which indicates that most of the 4-(dimethoxymethyl)phenylmagnesium bromide is still present after a total reaction time of 23 hours.

EXAMPLE 9

Preparation of 2-(tetrahydro-pyran-2-yl)-5-[4'-(tetrahydro-pyran-2-yloxymethyl)-biphenyl-2-yl]-2H-tetrazole

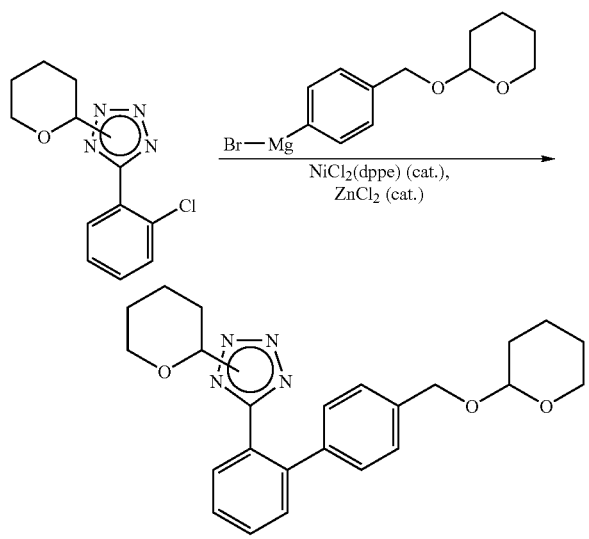

A suspension of magnesium turnings (0.48 g) in anhydrous tetrahydrofuran (13.5 mL) is cooled to 14° C., treated with a 25 weight % solution of diisobutylaluminium hydride in toluene (0.24 mL; 0.36 mmol) and stirred for 20 min. At 14° C., 2-(4-bromo-benzyloxy)tetrahydro-pyran (94.5% content; 0.26 g; 0.90 mmol) is added under vigorous stirring. After the reaction starts, more 2-(4-bromo-benzyloxy)-tetrahydro-pyran (94.5% content; 4.91 g; 17.1 mmol) is added over 40 minutes. The resulting mixture is further stirred at about 25° C. for 2.5 hours. The theoretical concentration of 4-(tetrahydro-pyran-2-yloxymethyl)phenyl-magnesium bromide in the solution above the excess of magnesium turnings is about 0.95 M. In another flask, a mixture of 5-(2-chlorophenyl)-2-(tetrahydropyran-2-yl)2H-tetrazole and 5-(2-chlorophenyl)-1-(tetrahydropyran-2-yl)-1H-tetrazole (94% content; 4.22 g; 15.0 mmol) is dissolved in anhydrous tetrahydrofuran (2.8 mL) under an inert atmosphere and dichloro[1,2-bis(diphenylphosphino)ethane]nickel(II) (80.8 mg; 0.15 mmol) and a 0.5 M zinc chloride solution in tetrahydrofuran (0.45 mL; 0.23 mmol) are added. The vigorously stirred resulting suspension is cooled to about 15° C. and the above 4-(tetrahydro-pyran-2-yloxymethyl)phenylmagnesium bromide solution (19 mL; 18 mmol) is added over one hour while keeping the temperature below 25° C. by external cooling. The brown reaction mixture is stirred at room temperature for 17.5 hours. After that, about 97% of the starting material are converted according to HPLC analysis. Methanol (1.2 mL; 30 mmol) is added to the mixture followed by isopropyl acetate (40 mL), a solution of ammonium chloride (0.4 g) in water (10 mL) and water (10 mL). The layers are separated. The organic layer is washed with water (10 mL) and three times with a solution of sodium hydrogencarbonate (1.0 g) in water (12 mL). The aqueous layer is extracted with isopropyl acetate (50 mL). The combined organic layers are washed twice with water (10 mL) and are evaporated in vacuo.

The resulting greenish oil is purified by column chromatography on silica gel eluting with a 1:4 mixture of ethyl acetate and hexane (in the presence of 0.3 volume-% of triethylamine) to afford the main isomer (N2-isomer) 2-(tetrahydro-pyran-2-yl)5-[4'-(tetrahydro-pyran-2-yloxymethyl) biphenyl-2-yl]-2H-tetrazole as a colorless oil.

Mass spectrum (ESI+): m/z=421 [M+H]$^+$ and m/z=438 [M+NH$_4$]$^+$.

EXAMPLE 10

Preparation of [2'-(1H-tetrazol-5-yl)biphenyl-4-yl]-methanol

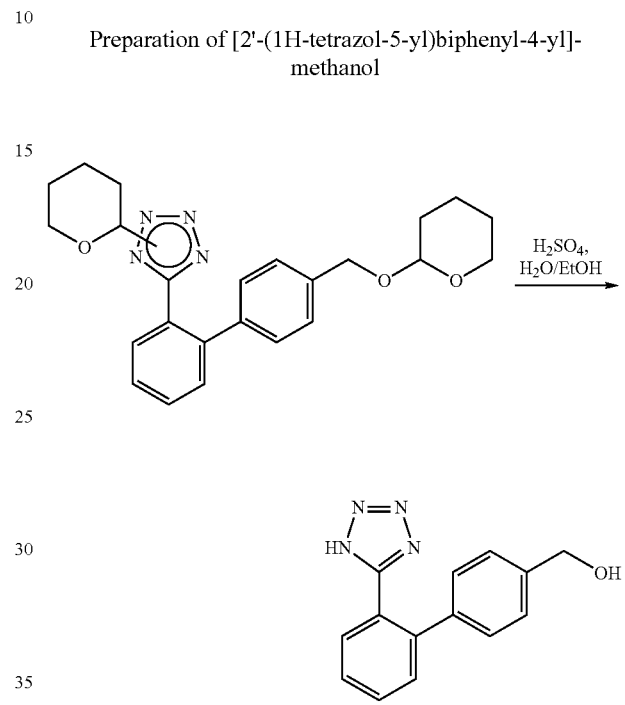

To 2-(tetrahydro-pyran-2-yl)-5-[4'-(tetrahydro-pyran-2-yloxymethyl)-biphenyl-2-yl]-2H-tetrazole (3.36 g; 8.00 mmol) are added 94% ethanol (12 mL) and a 2 M aqueous solution of sulfuric acid (1.0 mL; 2.0 mmol). The resulting mixture is heated to 45° C. for 3.5 hours. Water (16 mL) is slowly added and the mixture is allowed to cool down to room temperature. The pH of the reaction mixture is adjusted to pH 2 to 3 by adding a 2M aqueous sodium hydroxide solution (0.6 mL). The mixture is concentrated under reduced pressure, diluted with isopropyl acetate (15 mL) and washed three times with water (3 mL). The organic extract is concentrated under reduced pressure to a volume of about 4 mL and tert-butyl methyl ether (8 mL in total) is slowly added. The mixture is stirred overnight, diluted with a small amount of isopropyl acetate and further stirred for 4.5 hours. The suspended, white solid is filtered, washed with a small amount of isopropyl acetate and dried under reduced pressure to afford [2'-(1H-tetrazol-5-yl)-biphenyl-4-yl]-methanol. The filtrate is concentrated under reduced pressure, and tert-butyl methyl ether (3 mL) and heptane (0.5 mL) are slowly added. The mixture is stirred at room temperature overnight and at 0 to 5° C. for 1 hour. The suspended, white solid is filtered, washed with a small amount of isopropyl acetate and dried under reduced pressure to afford a second crop of [2'-(1H-tetrazol-5-yl)-biphenyl4-yl]-methanol.

Melting range: 132.4-134.6° C.

EXAMPLE 11

Preparation of 2'-(1H-tetrazol-5-yl)-biphenyl-4-carbaldehyde

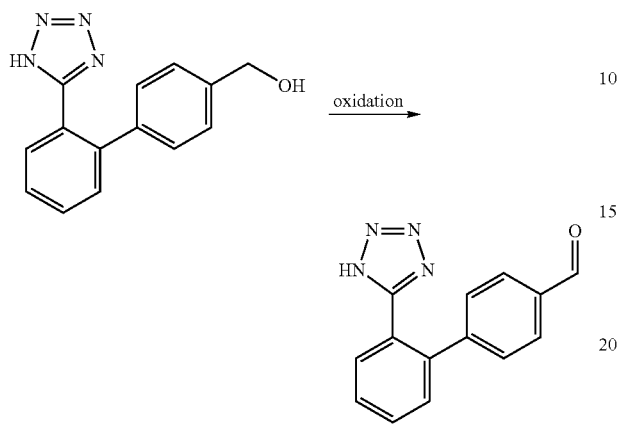

A mixture of [2'-(1H-tetrazol-5-yl)-biphenyl-4-yl]-methanol (1.03 g; 4.0 mmol), triethylamine (2.80 mL; 20 mmol) and dimethylsulfoxide (2 mL) is cooled to 12° C., and a solution of sulfur trioxide pyridine complex (1.27 g; 8.0 mmol) in dimethylsulfoxide (6.4 mL) is added over 10 minutes. The resulting clear solution is stirred at room temperature for almost 48 hours during which time more triethylamine (0.28 mL; 2.0 mmol) is added. The mixture is diluted with ethyl acetate (10 mL), cooled to 0 to 5° C. and slowly treated with a 2 M aqueous hydrochloric acid solution (15 mL). The aqueous layer is separated and extracted with ethyl acetate (10 mL). The combined organic layers are diluted with ethyl acetate (10 mL), washed with a 2 M aqueous hydrochloric acid solution (15 mL), twice with a 1 M aqueous hydrochloric acid solution (10 mL) and with a 10% aqueous solution of sodium chloride (10 mL). The organic extract is concentrated at 45° C. under reduced pressure to a volume of about 4 to 5 mL. The resulting suspension is stirred at room temperature for 45 minutes and at 0 to 5° C. for one hour before it is filtered. The solids are washed with cold ethyl acetate (2 mL) and dried at 45° C. under reduced pressure to give 2'-(1H-tetrazol-5-yl)-biphenyl-4-carbaldehyde as white, crystalline solid. A second crop can be obtained by concentrating the mother liquor to a volume of about 1 mL and filtering the solid formed.

Melting range: 188.2-189.3° C.

What is claimed is:

1. A process for the manufacture of the compound of formula (I)

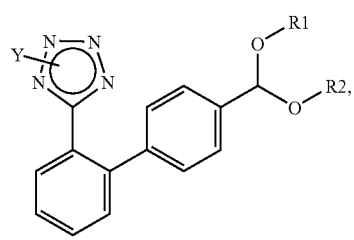

(I)

wherein Y represents a tetrazole protecting group, and $R_1$ and $R_2$, independently of one another, represent $C_1$-$C_{10}$-alkyl, or $R_1$ and $R_2$ combined together form $C_2$-$C_{10}$-alkylene; comprising reacting an aryl magnesium halide compound of formula (II b)

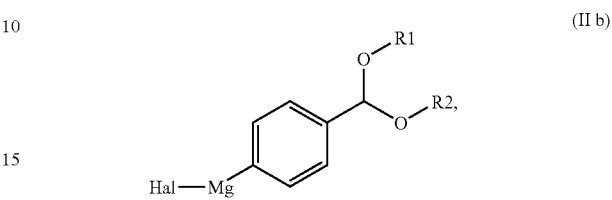

(II b)

wherein Hal is chlorine, bromine or iodine, in the presence of a transition metal catalyst and a catalytically effective amount of a metal salt additive, with a compound of formula (II c)

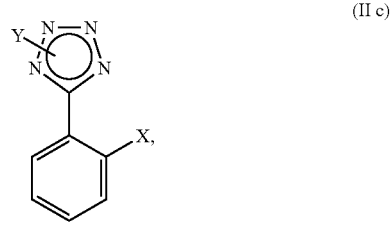

(II c)

wherein X is a substituent which, when bound to a phenyl ring, is not considerably replaceable at room temperature by an aryl magnesium halide reagent of formula (II b) in the absence of a catalyst; and, if necessary, isolating a resulting compound of formula (I).

2. A process according to claim 1, wherein an aryl magnesium halide reagent of formula (II b) is prepared by reacting a compound of formula (II a)

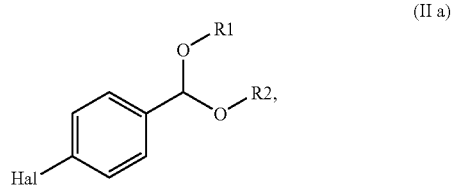

(II a)

wherein $R_1$, $R_2$ and Hal have meanings as defined in claim 1, with an active form of magnesium in an appropriate solvent.

3. A process according to claim 1, which process further comprises deprotecting a compound of formula (I) to afford a compound of formula (I A)

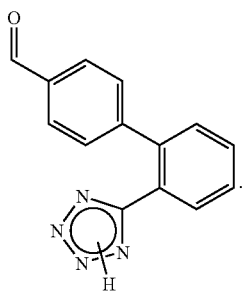

(I A)

4. A process according to claim 1, wherein variable Y is selected from the group consisting of 1-butoxyethyl, 1-ethoxyethyl, 2-tetrahydropyranyl and 2-tetrahydrofuranyl.

5. A process according to claim 1, wherein a transition metal catalyst is a complex of a transition metal or a transition metal salt and one, two or up to four coordinating ligands selected from the group consisting of triphenylphosphine, tri(ortho-tolyl)phosphine, tri(para-tolyl)phosphine, trimethylphosphine, triethylphosphine, tributylphosphine, tri(1,1-dimethylethyl)phosphine, tricyclopentylphosphine, tricyclohexylphosphine, trimethylphosphite, triethylphosphite, tri(1-methylethyl)phosphite, tricyclopentylphosphite, tricyclohexylphosphite, 1,2-bis(diphenylphosphino)ethane, 1,3-bis(diphenylphosphino)propane, 1,4-bis(diphenylphosphino)butane, 1,1'-bis(diphenyl-phosphino)ferrocene, 1,1'-bis(di-[2-propyl]-phosphino)ferrocene, 1,1'-bis(di-tert-butyl-phosphino)ferrocene, 1,2-bis(diphenylphosphino)benzene, 2,2'-bis(diphenylphosphino)-1,1'-biphenyl, 2,2'-bis(diphenylphosphino)-1,1'-binaphtyl, bis(2-diphenylphosphinophenyl)ether and 9,9-dimethyl-4,5-bis(diphenylphosphino)xanthene.

6. A process according to claim 5, wherein a transition metal salt is selected from the group consisting of nickel(II) chloride, nickel(II) bromide and nickel(II) acetylacetonate.

7. A process according to claim 5, wherein a transition metal catalyst is selected from the group consisting of dichlorobis(triphenylphophine)nickel(II), dichloro[1,2-bis(diphenylphosphino)ethane]nickel(II) and dichloro[1,3-bis(diphenylphosphino)propane]- nickel(II).

8. A process according to claim 5, wherein a transition metal salt is selected from the group consisting of palladium (II) chloride, palladium(II) bromide and palladium(II) acetate.

9. A process according to claim 5, wherein a transition metal catalyst is selected from the group consisting of dichlorobis(triphenylphophine)palladium(II), dichloro[1,3-bis (diphenylphosphino)propane]palladium(II) and dichlorof[1, 1'-bis(diphenylphosphino) -ferrocene]palladium(II), or a dichloromethane adduct thereof.

10. A process according to claim 1, wherein a metal salt additive is selected from the group consisting of a copper(I), copper(II), zinc(II), silver(I), cadmium(II), mercury(II), aluminum(III), gallium(III), indium(III), tin(IV), titanium(IV) and zirconium(IV) salt.

11. A process according to claim 10, wherein the amount of metal salt additive used is between 0.1 and 8 molar % relative to a compound of formula (II c).

12. A process according to claim 1, wherein X is chlorine; and a transition metal catalyst is a complex of nickel(0), or a complex of nickel(II) salt with at least one organophosphorus compound containing trivalent phosphorus; or a transition metal catalyst is a nickel(II) complex with an organophosphorus ligand which contains two trivalent phosphorus atoms.

13. A process according to claim 12, wherein a transition metal catalyst is dichloro[1,2-bis(diphenylphosphino) ethane]nickel(II); and a metal salt additive is $ZnCl_2$ or $ZnBr_2$.

14. A process according to claim 1, wherein X is bromine; and a transition metal catalyst is a complex of palladium(0), or a complex of a palladium(II) salt with at least one organophosphorus compound containing trivalent phosphorus; or a transition metal catalyst is a palladium(II) complex with an organophosphorus ligand which contains two trivalent phosphorus atoms.

15. A process according to claim 14, wherein a transition metal catalyst is dichloro[1,1'-bis(diphenylphosphino)ferrocene]palladium(II), or a dichloromethane adduct thereof; and a metal salt additive is $ZnCl_2$ or $ZnBr_2$.

16. A process according to claim 1, wherein a transition metal catalyst is an uncomplexed transition metal which is selected from the group consisting of nickel, palladium, platinum, cobalt, manganese or copper; or wherein a transition metal catalyst is an uncomplexed transition metal salt which is selected from the group consisting of nickel(II), palladium (II), platinum(II), cobalt(II), manganese(II), copper(I) or copper (II) chloride, bromide, iodide, hydroxide, oxide, acetate, hydroxyacetate, propionate, succinate, trifluoroacetate, acetylacetonate, nitrate, cyanide, sulfate, trifluoromethanesulfonate, methanesulfonate, benzenesulfonate or p-toluenesulfonate thereof.

* * * * *